(12) United States Patent
Navia

(10) Patent No.: US 7,488,346 B2
(45) Date of Patent: Feb. 10, 2009

(54) METHOD AND APPARATUS FOR REPLACING A MITRAL VALVE AND AN AORTIC VALVE WITH A SINGLE HOMOGRAFT

(75) Inventor: Jose Luis Navia, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 282 days.

(21) Appl. No.: 11/037,499

(22) Filed: Jan. 18, 2005

(65) Prior Publication Data

US 2005/0187617 A1 Aug. 25, 2005

Related U.S. Application Data

(60) Provisional application No. 60/537,838, filed on Jan. 21, 2004.

(51) Int. Cl.
*A61F 2/24* (2006.01)
(52) U.S. Cl. ..................... 623/1.26; 623/904
(58) Field of Classification Search ............... 623/1.26, 623/2.12–2.19, 14.13, 904, 918, 922, 23.72–23.76
See application file for complete search history.

(56) References Cited

U.S. PATENT DOCUMENTS

| | | | |
|---|---|---|---|
| 4,790,844 A | 12/1988 | Ovil | |
| 4,960,424 A | 10/1990 | Grooters | |
| 5,156,621 A | 10/1992 | Navia et al. | |
| 5,163,954 A | 11/1992 | Curcio et al. | |
| 5,344,442 A | 9/1994 | Deac | |
| 5,415,667 A | 5/1995 | Frater | |
| 5,500,015 A | 3/1996 | Deac | |
| 5,554,184 A | 9/1996 | Machiraju | |
| 5,733,331 A | 3/1998 | Peredo | |
| 5,824,067 A | 10/1998 | Gross | |
| 5,928,281 A | 7/1999 | Huynh et al. | |
| 6,074,417 A | 6/2000 | Peredo | |
| 6,312,464 B1 | 11/2001 | Navia | |
| 6,358,277 B1 | 3/2002 | Duran | |
| 6,409,759 B1 | 6/2002 | Peredo | |
| 6,524,339 B1 | 2/2003 | Adams | |
| 2002/0052651 A1 | 5/2002 | Myers et al. | |
| 2002/0091441 A1 | 7/2002 | Guzik | |

(Continued)

OTHER PUBLICATIONS

Pomar, et al. Management of Persistent Tricuspid Endocarditis with Transplantation of Cryopreserved Mitral Homografts, *The Journal of Thoracic and Cardiovascular Surgery*, 1994;107:1460-1463.

(Continued)

*Primary Examiner*—Suba Ganesan
(74) *Attorney, Agent, or Firm*—Tarolli, Sundheim, Covell & Tummino LLP

(57) ABSTRACT

A method and apparatus for replacing both the native mitral valve and the native aortic valve in a heart with a stentless bioprosthetic graft is provided. The bioprosthetic graft comprises a harvested homograft that includes a mitral valve portion and an aortic valve portion, and an extension portion made of a biocompatible material. The extension portion is sutured to the homograft and is for suturing to the left atrial wall of the heart to close an incision in the left atrial wall following implantation of the mitral valve portion and the aortic valve portion of the homograft.

5 Claims, 8 Drawing Sheets

U.S. PATENT DOCUMENTS

2003/0069635 A1    4/2003    Cartledge et al.
2004/0122512 A1    6/2004    Navia et al.
2004/0122513 A1    6/2004    Navia et al.

OTHER PUBLICATIONS

Acar et al. Surgery for Acquired Heart Disease, *The Journal of Thoracic and Cardiovascular Surgery*, 1996;111:367-380.

Walther et al. Stentless Tricuspid Valve Replacement, *Ann Thorac Surg.*, 1999;68:1858-60.

Hvass et al. Mitral Homografts for Total Tricuspid Valve Replacement: Comparison of Two Techniques, *The Journal of Thoracic and Cardiovascular Surgery*, 2001;121:592-594.

Obadia et al. Monobloc Aorto-Mitral Homograft as a Treatment of Complex Cases of Endocarditis, The Journal of Thoracic and Cardiovascular Surgery, 2001;121:584-586.

Obadia et al. Monobloc Aorto-Mitral Homograft or Mechanical Valve Replacement: A New Surgical Option for Extensive Bivalvular Endocarditis, *The Journal of Thoracic and Cardiovascular Surgery*, 2006;131:243-245.

Revuelta et al. Transvalvular Technique for Implantation of a Mitral Valve Homograft, *The Journal of Thoracic and Cardiovascular Surgery*, 1996;111:281-282.

Author: Tirone E. David, undated, Chapter 33 entitled "Surgical Treatment of Aortic Valve Endocarditis", pp. 857-865.

Author: Fann et al., undated, Chapter 36 entitled "Pathophysiology of Mitral Valve Disease", pp. 901-905.

Dagum et al., "Functional Evaluation of the Medtronic Stentless Porcine Xenograft Mitral Valve in Sheep", *Circulation.* 1999; 100[suppl II]:II-70-II-77.

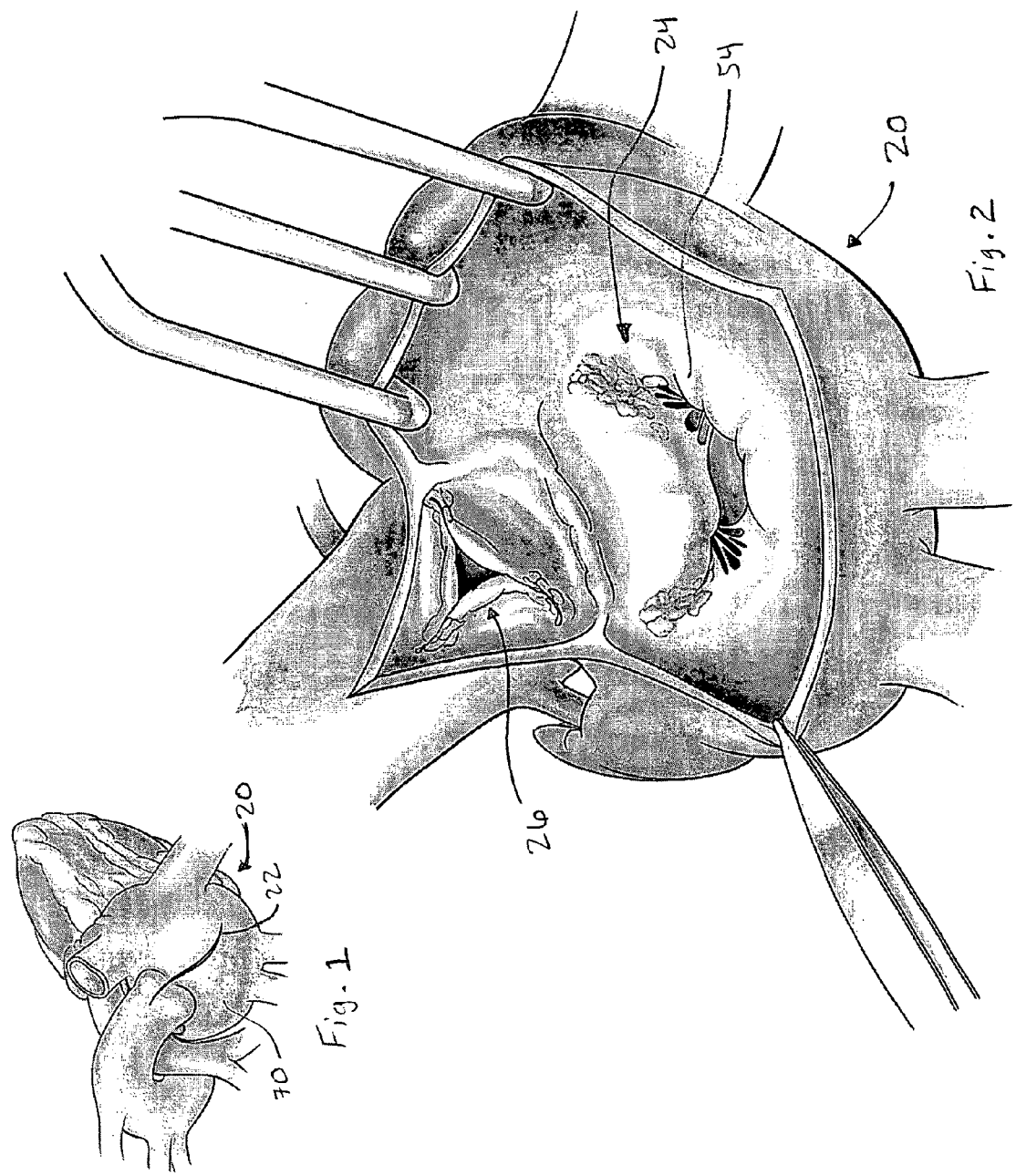

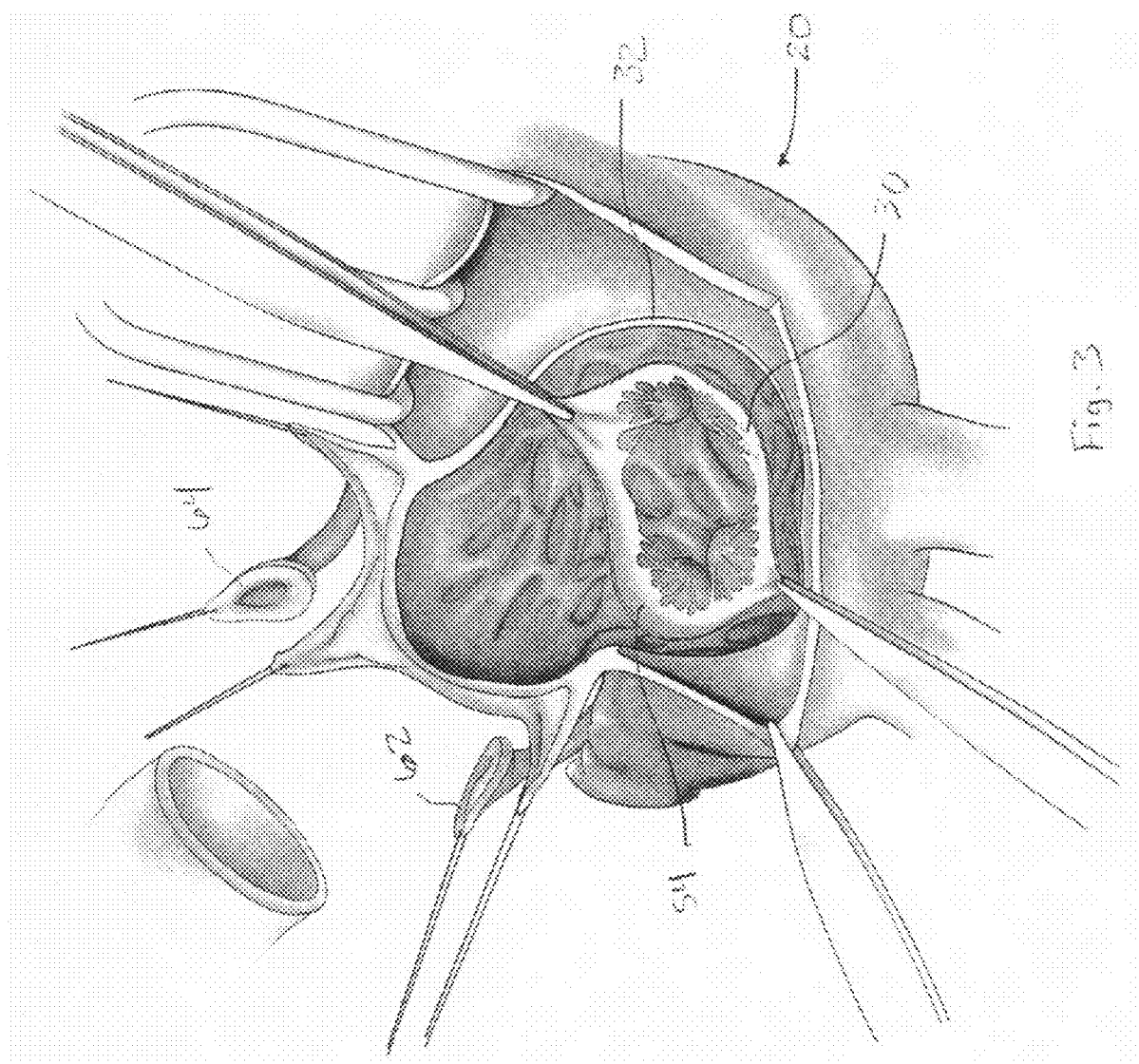

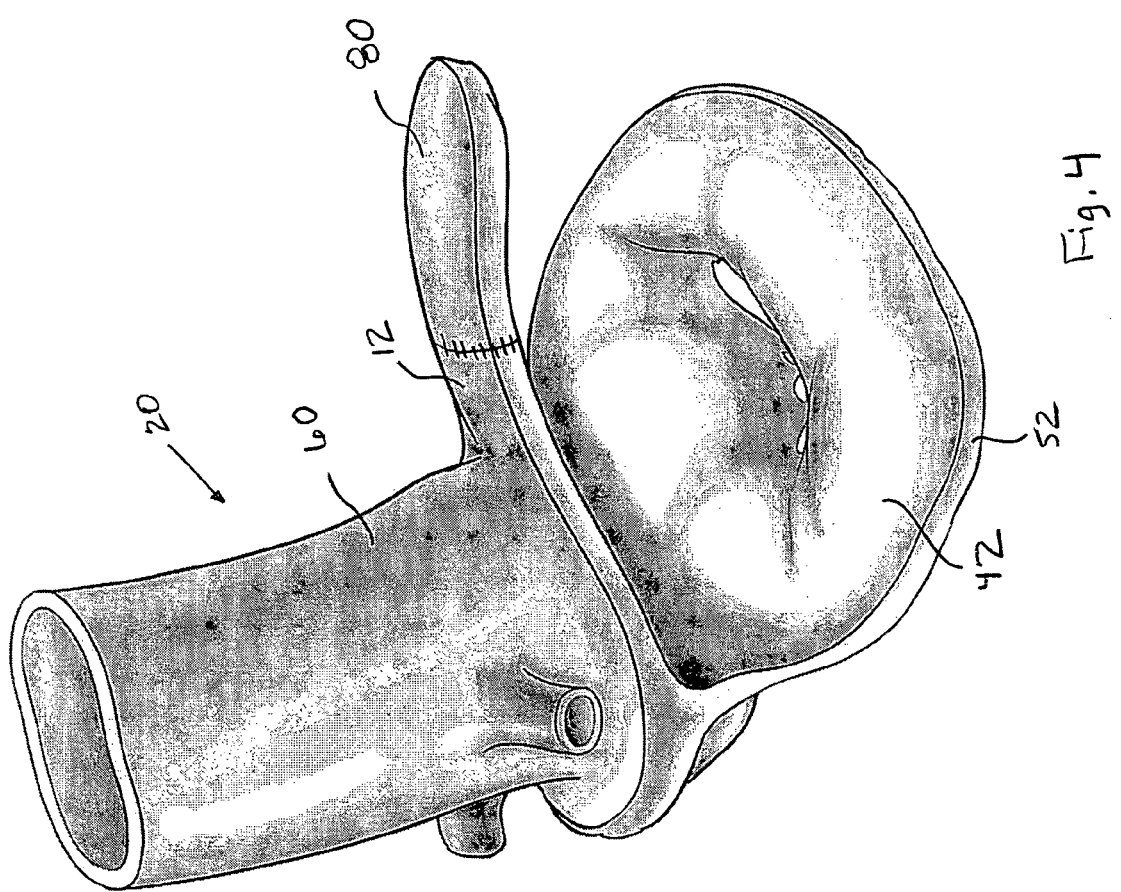

METHOD AND APPARATUS FOR REPLACING A MITRAL VALVE AND AN AORTIC VALVE WITH A SINGLE HOMOGRAFT

RELATED APPLICATIONS

The present application claims priority from U.S. Provisional Patent Application No. 60/537,838, filed Jan. 21, 2004, which is herein incorporated by reference in its entirety.

TECHNICAL FIELD

The present invention relates to a method and apparatus for replacing both a mitral valve and an aortic valve with a single homograft.

BACKGROUND OF THE INVENTION

It is known to replace a diseased mitral valve with a stented or unstented bioprosthetic valve. The bioprosthetic mitral valve can be made from a harvested biological tissue including bovine, equine or porcine pericardial tissue, a bovine, equine or porcine mitral valve, or a homograft (or allograft) mitral valve. The bioprosthetic mitral valve can also be made from a suitable synthetic material including such as polyurethane or expanded PTFE.

It is also known to replace a diseased aortic valve with a stented or unstented bioprosthetic valve. The bioprosthetic aortic valve can be made from a harvested biological tissue including bovine, equine or porcine pericardial tissue, bovine, equine or porcine aortic valve, or a homograft (or allograft) aortic valve. The bioprosthetic aortic valve can also be made from a suitable synthetic material such as polyurethane or expanded PTFE.

In some cases, both the mitral valve and the aortic valve are diseased and a need exists for a method and apparatus for replacing both valves with a single bioprosthetic implantation in a single procedure. The present invention addresses this need using a single, stentless homograft.

SUMMARY OF THE INVENTION

The present invention is a stentless bioprosthetic graft for replacing both the native mitral valve and the native aortic valve in a heart. The bioprosthetic graft comprises a harvested homograft that includes a mitral valve portion and an aortic valve portion, and an extension portion made of a biocompatible material. The extension portion is sutured to the homograft and is for suturing to the left atrial wall of the heart to close an incision in the left atrial wall following implantation of the mitral valve portion and the aortic valve portion of the homograft.

In accordance with one aspect of the invention, the mitral valve portion of the homograft includes first and second leaflets for suturing to free edges of the anterior and posterior leaflets of the native mitral valve that are left intact following resection of the native mitral valve so that the native primary and secondary chordae tendinea, which are attached to the papillary muscles, continue to provide prolapse prevention and left ventricular muscle support functions in addition to maintaining the continuity between the valve annulus and the papillary muscles.

The present invention further provides a method for replacing a native mitral valve and a native aortic valve with a single bioprosthetic graft.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a view of the recipient heart showing an incision in preparation for the excising of the native mitral and aortic valves;

FIG. 2 is a view of the recipient heart with the diseased native mitral and aortic valves exposed for excision;

FIG. 3 is a view of the recipient heart following excision of the diseased native mitral and aortic valves and illustrates that the free edges of the leaflets of the native mitral valve are preserved along with the native chordae tendinea;

FIG. 4 is a view of a harvested mitral and aortic valve homograft for implantation into the recipient heart;

DESCRIPTION OF EMBODIMENTS

Figure 5:
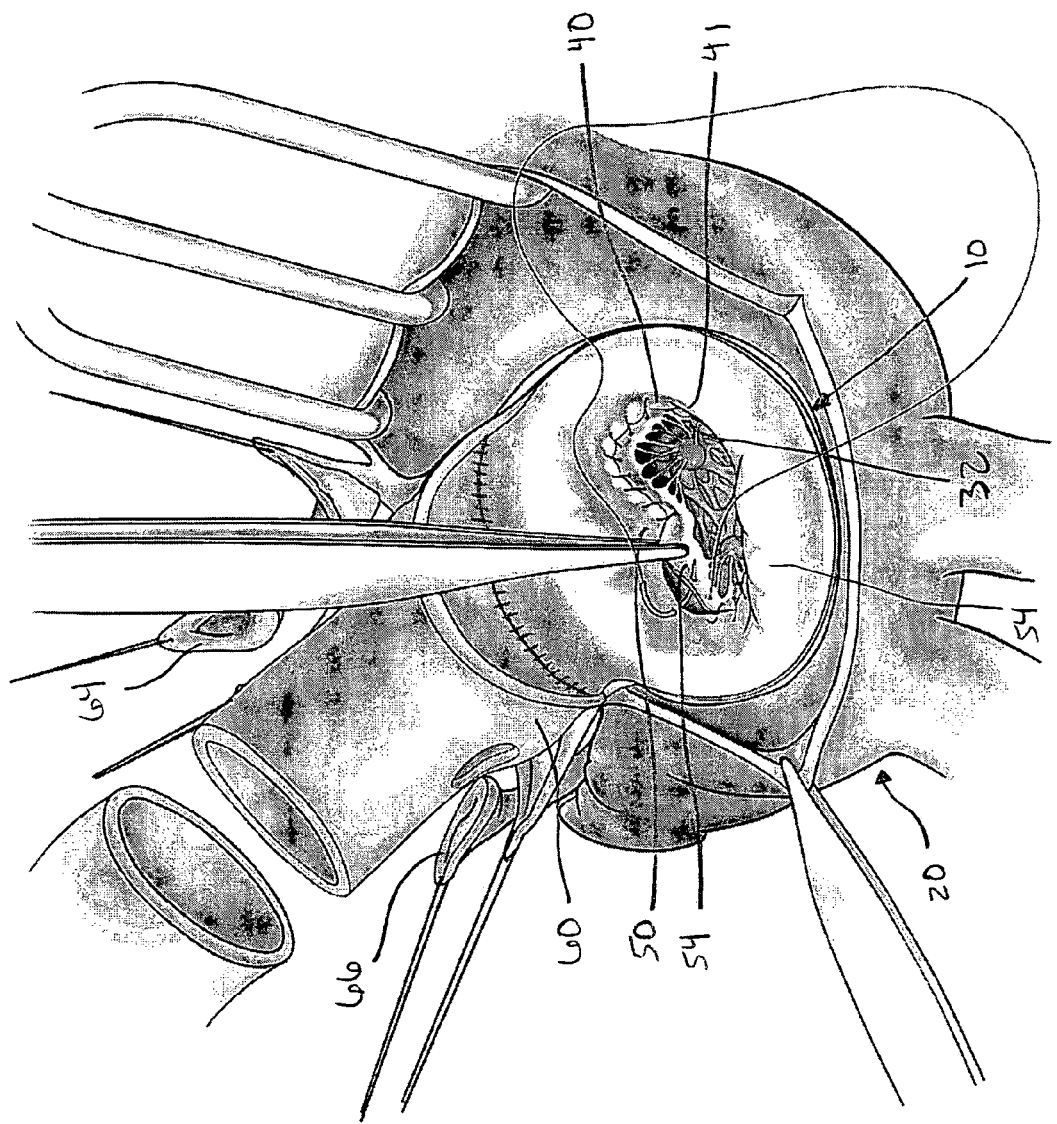
FIG. 5 is a view illustrating the mitral valve portion of the homograft being sutured to the free edges of the native valve leaflets.

The present invention relates to a method and apparatus for replacing both a mitral valve and an aortic valve with a single homograft.

Prior to implantation into a recipient heart, the homograft is harvested as described below. First, the left atrium of a donor heart (not shown) is opened in a manner such that the dome at the level of the aortic root is preserved. The mitral annulus, leaflets, and subvalvular apparatus are then anatomically evaluated. Next, the mitral valve's anterior and posterior leaflet heights are measured. The distal ascending aorta is then transected and the aortic valve, the two coronary ostiums, and the ascending aorta are anatomically evaluated and measured.

Next, the left ventricle is opened below the papillary muscle level (not shown). The entire mitral valve is then excised or removed by incision of the valve circumferentially. The incision is placed near the fibrous annulus of the valve and around the posterior area of the annulus, taking care to preserve the aortic-mitral membrane, the ascending aorta, the dome of the left atrium at the reflection of the aortic root, and the mitral valve annulus intact as a single unit. The chordae tendinea that remain attached to the valve leaflets are then removed along with the tips of the papillary muscles. The aortic-mitral valve homograft can then be frozen or otherwise preserved for implantation.

After the aortic-mitral valve homograft is thawed for implantation, the excess myocardium is trimmed. The myocardium of the atrium and the ventricle is cut away from the mitral and aortic valve annulus without damaging the leaflets, leaving behind just enough tissue to allow sewing both the homograft annulus and the dome of the left atrial wall area at the aortic root junction level. The chordae tendinea and the papillary muscles can then be preserved in a standard fashion for attachment to the left ventricular wall in a known manner (see, for e.g., U.S. Pat. No. 6,074,417 to Peredo).

Alternatively, the chordae tendinea and the papillary muscles can be trimmed from the free-edges of both leaflets of the mitral valve homograft. This alternative technique leaves the free edges intact so that they may be attached to the native free-edge leaflets in accordance with U.S. patent application Ser. No. 10/683,105 ("the '105 patent application"), entitled METHOD AND APPARATUS FOR REPLACING A MITRAL VALVE WITH A STENTLESS BIOPROSTHETIC VALVE, filed on Oct. 10, 2003 and issued Aug. 8, 2006, as U.S. Pat. No. 7,087,079, the subject matter of which is incorporated herein by reference.

It is further contemplated that the technique for leaving the free edges described in the '105 patent application could be used on only the native anterior leaflet so that the native posterior leaflet is preserved.

As shown in FIG. 4, a left atrial wall portion 12 of the homograft 10 is then extended by attaching an extension piece 80 made of autologous or heterologous pericardium or other biological tissue. The extension piece 80 could alternatively be made of a biocompatible artificial tissue. The extension piece 80 can either be attached to the homograft 10 at the time of harvesting of the homograft or prior to implantation of the homograft. It should be noted that the homograft 10, including the extension piece 80 attached thereto, can be either cryopreserved or tanned (fixed) as known in the art following its harvest.

Based on the direct or echocardiographic measurements of the native aortic and mitral valve size, the leaflets heights, and the subvalvular apparatus, a particular aortic-mitral homograft 10 (FIG. 4) is chosen for implantation in a recipient heart 20 (FIG. 1). An incision 22 (FIG. 1) is made to open the left atrium. As shown in FIG. 2, the incision allows exposure of the native mitral valve 24 and the native aortic valve 26 of the recipient heart 20 for excision. The native aortic valve 26 is then excised in a known manner. Next, the native mitral valve 24 is excised (see FIG. 3) in accordance with the technique described in the '105 patent application, wherein the native anterior leaflet is dissected from the mitral annulus 30 and the clear zone of the anterior leaflet is resected. It is important that the rough zone and the free edge 32 of the native anterior leaflet, the strut chordae, and the rough zone chordae are preserved.

The mitral-aortic homograft 10 (FIG. 4) is then moved into position for implantation. As shown in FIG. 5, the free edge 40 of the anterior leaflet 41 of the mitral valve portion 42 of the homograft 10 is sutured down to the native anterior leaflet 32 with 5-0 Ethibond or polypropylene (Prolene 5-0) continuous over-and-over sutures. This suture is usually started from the apex (or middle) of the anterior leaflet 41 toward both commissural sides, which makes it easy to suture the homograft 10 to the native anterior leaflet 32 precisely without any leaflet folds. The same procedures are repeated for the attachment of the homograft's posterior leaflet 50 on the native posteromedial scallop and both posterolateral scallops on the posterior leaflet 54. During these procedures for the posterior leaflet, the rough zone and the free edge of the native posterior leaflets, the rough zone chordae, and the cleft chordae (except for the basal chordae) must be preserved.

Figure 6:
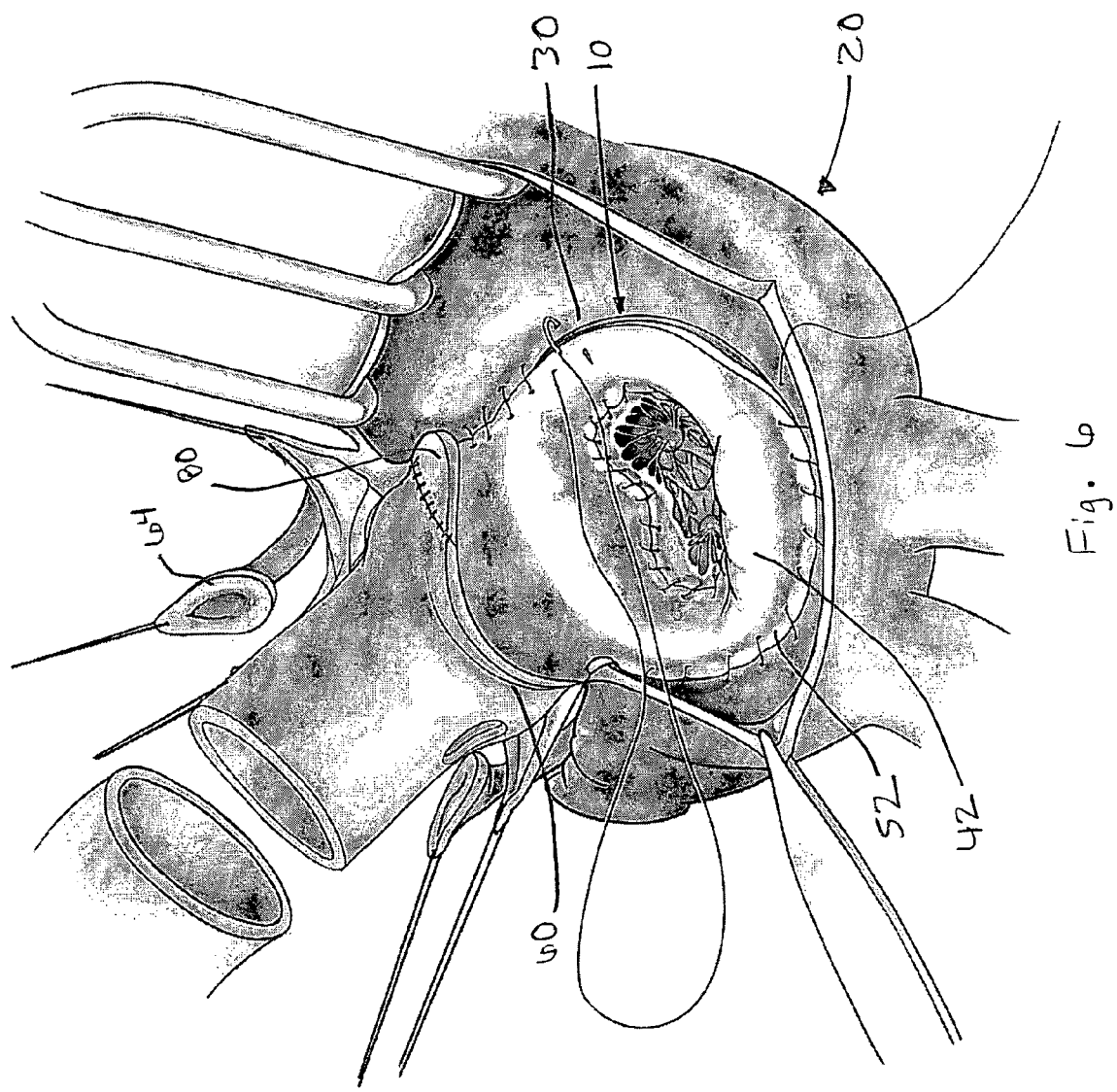
FIG. 6 is a view illustrating the proximal end of the mitral valve portion of the homograft being sutured to the valve annulus.

The annulus 52 of the mitral valve portion 42 of the homograft 10 is then sutured down to the native mitral annulus 30 using continuous stitches of 4-0 polypropylene sutures as shown in FIG. 6. The fibrous trigones of the homograft 10 are lined up with the patient's fibrous trigones. Attention is given to distributing the graft leaflet tissue uniformly around the mitral annulus 30. The mitral valve portion 42 of the homograft 10 can be supported by remodeling annuloplasty using a partial or complete annuloplasty mitral ring (not shown) that is sized to match the size of the homograft's anterior leaflet 32. The annuloplasty ring is secured with sutures placed around the posterior inter-trigonal perimeter of the native mitral annulus 30.

It should be noted that the standard mitral valve homograft-papillary muscle technique (ref. U.S. Pat. No. 6,074,417 to Peredo) can also be used to implant the mitral valve homograft 10.

Figure 7:
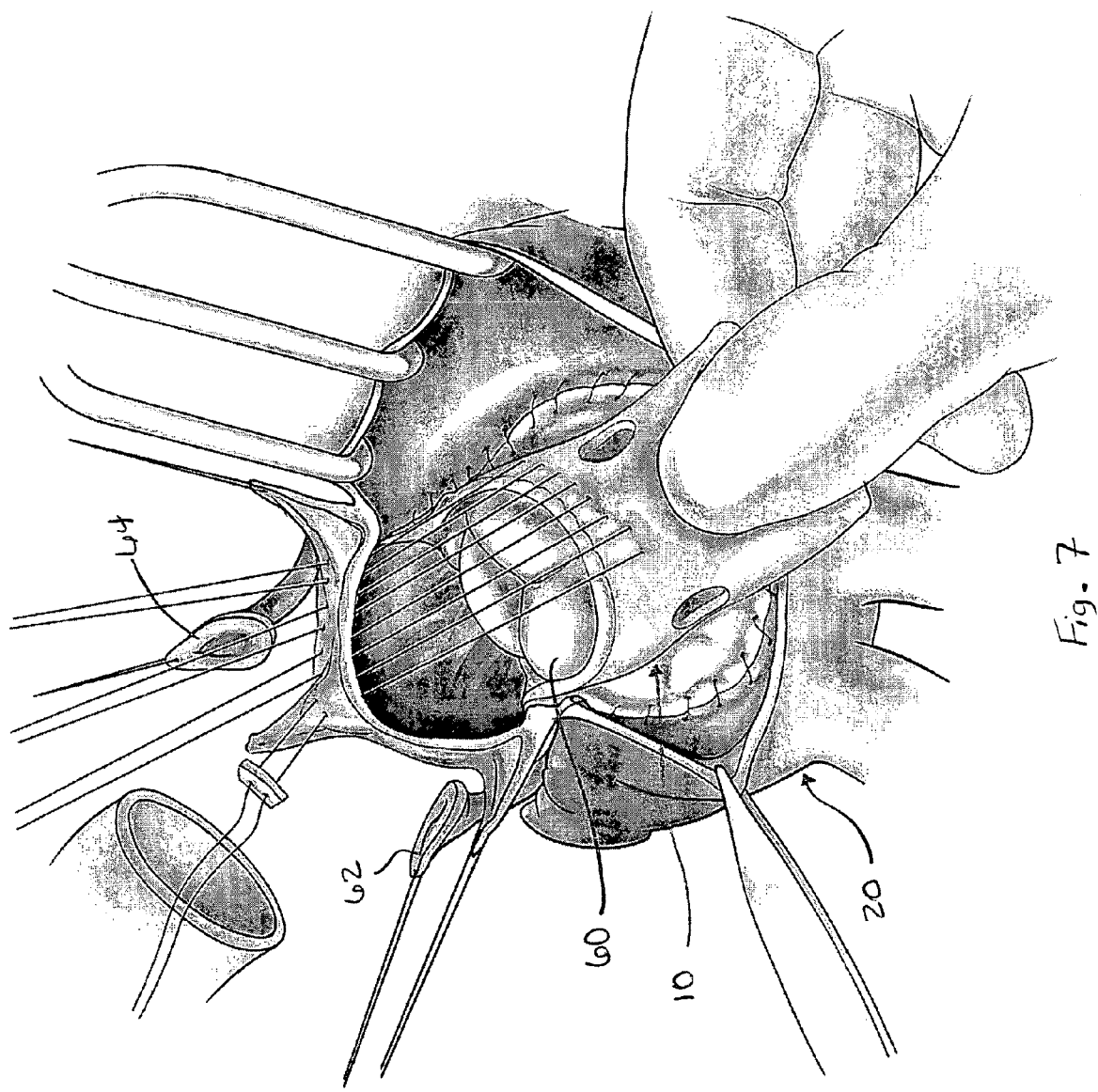
FIG. 7 is a view illustrating the aortic valve portion of the homograft being sutured in place.
Figure 8:
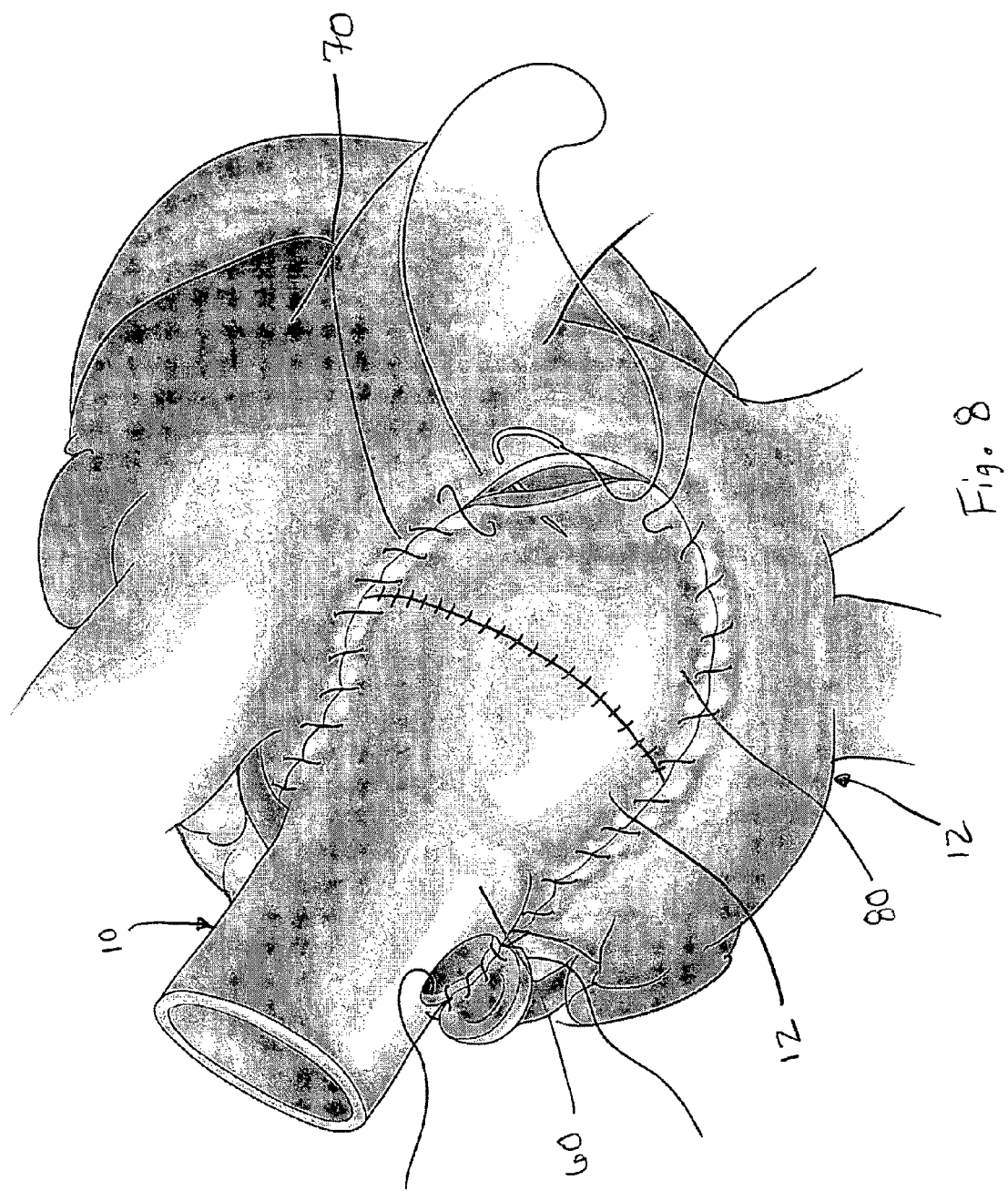
FIG. 8 is a view illustrating the coronary ostiums being sutured to the aortic wall and the left atrium being closed with an extension portion of the homograft.
Figure 9:
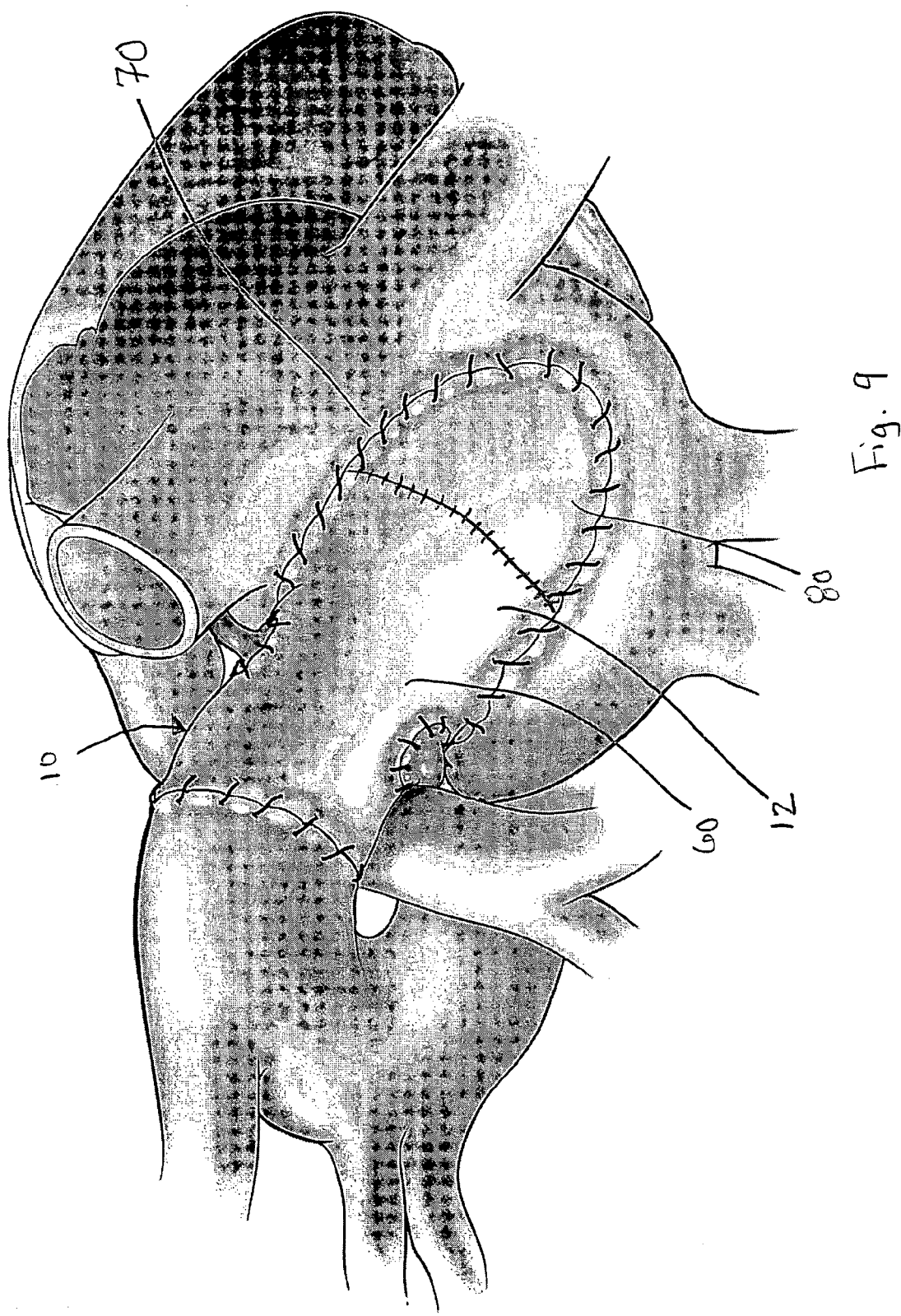
FIG. 9 is a view of the recipient heart following implantation of the homograft.

The aortic valve portion 60 of the homograft is then implanted in a known manner using a procedure referred to as a "Mini Root Technique" shown in FIG. 7. Finally, as shown in FIGS. 7 and 8, the native coronary ostium buttons 62 and 64 are attached to the homograft's aortic wall with 4-0 or 5-0 polypropylene sutures, and the dome of the left atrial wall 70 of the recipient heart 20 is closed using the extension piece 80 of the homograft 10. An exterior view of the recipient heart 20 following implantation of the mitral-aortic homograft 10 according to the present invention is shown in FIG. 9.

From the above description of the invention, those skilled in the art will perceive improvements, changes and modifications. Such improvements, changes and modifications within the skill of the art are intended to be covered by the appended claims.

Having described the invention, I claim:

1. A method for replacing a native mitral valve and a native aortic valve with a single bioprosthetic graft, said method comprising the steps of:

harvesting a homograft that includes both a mitral valve portion and an aortic valve portion;

resecting the native mitral and aortic valves from the heart;

suturing a biocompatible extension portion to the homograft;

suturing a free edge of at least one of an anterior leaflet and a posterior leaflet of the mitral valve portion of the homograft to at least one of a native anterior leaflet and a native posterior leaflet of the native mitral valve with the at least one of the anterior and posterior leaflets being operatively attached to at least one native chordae tendinae through the at least one native anterior and posterior leaflets;

suturing the aortic valve portion of the homograft in place of the native aortic valve; and suturing the extension portion to the left atrial wall of the heart to close the left atrial wall.

2. The method of claim 1, wherein the homograft includes an aortic wall, and the heart has at least one native coronary ostium button, and including the step of attaching at least one of the native coronary ostium buttons to the aortic wall during implantation of the homograft.

3. The method of claim 1, wherein at least one of the mitral valve portion and the aortic valve portion of the homograft has an annulus with associated myocardium, and including the step of trimming at least a portion of the myocardium from at least one annulus before implantation.

4. The method of claim 1, wherein the homograft includes at least one fibrous trigone, and including the step of aligning the fibrous trigone with a native fibrous trigone of the heart during implantation.

5. A method for replacing a native mitral valve and a native aortic valve with a single bioprosthetic graft, the native mitral valve including native anterior and posterior leaflets having corresponding native chordae tendinea, said method comprising the steps of:

harvesting a homograft that includes both a mitral valve portion and an aortic valve portion;

resecting at least a portion of the native aortic valve from the heart;

partially resecting the native mitral valve from the heart while maintaining at least one native free-edge leaflet attached to at least one native chordae tendinea;

suturing a biocompatible extension portion to the homograft;

suturing at least one of an anterior leaflet and a posterior leaflet of the mitral valve portion of the homograft to at least one native free-edge leaflet of the native mitral valve with the at least one of the anterior and posterior leaflets being operatively attached to at least one native chordae tendinae through the at least one native free-edge leaflet;

suturing the aortic valve portion of the homograft in place of the native aortic valve; and suturing the extension portion to the left atrial wall of the heart to close the left atrial wall.

* * * * *